United States Patent [19]

Herrmann et al.

[11] Patent Number: 4,734,219

[45] Date of Patent: Mar. 29, 1988

[54] STABILIZATION OF AQUEOUS ACIDIC SCRUBBING LIQUORS

[75] Inventors: Guenter Herrmann, Heidelberg; Ekhart Lucas, Wachenheim, both of Fed. Rep. of Germany

[73] Assignee: BASF Aktiengesellschaft, Ludwigshafen, Fed. Rep. of Germany

[21] Appl. No.: 886,603

[22] Filed: Jul. 18, 1986

[30] Foreign Application Priority Data

Jul. 24, 1985 [DE] Fed. Rep. of Germany ....... 3526412

[51] Int. Cl.$^4$ .................. C09K 15/02; C07C 51/31; C07C 51/42
[52] U.S. Cl. ................. 252/400.54; 562/579; 562/580; 562/590; 562/593; 562/606; 562/543
[58] Field of Search ............. 252/400.54; 422/12, 422/19; 568/366; 562/593, 606, 579, 580, 590, 543

[56] References Cited

U.S. PATENT DOCUMENTS

| | | |
|---|---|---|
| 2,031,632 | 6/1934 | Bottoms .................. 252/400.54 X |
| 2,617,835 | 11/1952 | Curtin, Jr. .................... 562/543 X |
| 2,938,924 | 5/1960 | Simon et al. .................... 568/358 |
| 3,340,304 | 9/1967 | Schulz et al. ................ 562/543 X |
| 3,439,041 | 4/1969 | Gey et al. ......................... 568/366 |
| 3,654,355 | 4/1972 | Mueller et al. .................... 562/543 |
| 3,892,780 | 7/1975 | Crowther et al. ................ 549/256 |
| 3,928,452 | 12/1975 | Brunie et al. .................... 568/342 |
| 3,983,208 | 9/1976 | Blay ..................................... 423/27 |
| 4,163,027 | 7/1979 | Magnussen et al. ............... 568/366 |
| 4,250,118 | 2/1981 | van de Mond et al. ...... 568/366 X |
| 4,341,907 | 7/1982 | Zelonka ........................... 568/360 |
| 4,465,861 | 8/1984 | Hermolin ......................... 568/342 |
| 4,562,295 | 12/1985 | Miyata ............................. 568/366 |

*Primary Examiner*—Matthew A. Thexton
*Attorney, Agent, or Firm*—Keil & Weinkauf

[57] ABSTRACT

Aqueous acidic scrubbing liquors obtained when oxidation mixtures from the oxidation of cyclohexane are scrubbed with water are stabilized by a process in which the scrubbing liquors are heated at from 50° to 130° C. in the presence of a water-soluble vanadium compound.

4 Claims, No Drawings

STABILIZATION OF AQUEOUS ACIDIC SCRUBBING LIQUORS

The present invention relates to a process for the stabilization of aqueous acidic scrubbing liquors from the oxidation of cyclohexane.

The oxidation of cyclohexane with molecular oxygen or with a gas containing this gives not only cyclohexanol and cyclohexanone but also acidic and other by-products, which have to be separated off from the reaction mixture before the desired products are recovered. Such water-soluble by-products are separated off by washing the oxidation mixture with water. The aqueous acidic scrubbing liquors contain carboxylic acids, such as adipic acid, hydroxycarboxylic acids and other, unidentified components. These acidic scrubbing liquors are usually further processed to obtain, for example, the adipic acid present therein. To do this, the said scrubbing liquors are collected in large tanks and transported to the site where further processing is carried out. To prevent solids from separating out, such solutions are kept at elevated temperatures, for example at 80° C. It has been found that such acidic scrubbing liquors release, per kg of the solution, from 0.4 to 2.5 l of a gas consisting predominantly of hydrogen. Such gases mix with atmospheric oxygen to give explosive mixtures which constitute a considerable hazard both during storage and during transport of the acidic scrubbing liquors.

It is an object of the present invention to provide a process for the stabilization of aqueous acidic scrubbing liquors from the oxidation of cyclohexane, the said process preventing the formation of hydrogen-containing gases.

We have found that this object is achieved by a process for the stabilization of aqueous acidic scrubbing liquors which were obtained by washing oxidation mixtures from the oxidation of cyclohexane, wherein the scrubbing liquor is heated at from 50° to 130° C. in the presence of a water-soluble vanadium compound.

The novel process has the advantage that the formation of hydrogen is prevented, and the source of danger during storage and transport of such scrubbing liquors is eliminated.

According to the invention, the aqueous acidic scrubbing liquors used are those obtained when oxidation mixtures from the oxidation of cyclohexane are washed with water. Such oxidation mixtures are obtained by oxidation of cyclohexane with molecular oxygen or with a gas containing this, eg. air, in the liquid phase at from 130° to 200° C. and under from 5 to 25 bar, in the presence or absence of a catalyst. The oxidation is carried out as a rule in a plurality of stages, eg. from 2 to 5 stages. The total amount of oxidation mixture thus obtained is washed with water after each stage, during the stages or after the final stage, in order to remove the acidic components. Scrubbing is carried out as a rule at from 80° to 140° C. under from 10 to 25 bar. The acidic scrubbing liquor is then separated off from the remaining cyclohexane oxidation mixture by a conventional method, for example decanting. Typical aqueous acidic scrubbing liquors contain in total, for example, from 10 to 20% by weight of dicarboxylic acids, such as adipic acid, and moncarboxylic acids, such as valeric acid and hydroxycaproic acid, and other unidentified by-products. In general, the acidic scrubbing liquors have an acid number of from 50 to 150.

According to the invention, water-soluble vanadium compounds are added to the said scrubbing liquors. Examples of suitable vanadium compounds are sodium vanadate, potassium vanadate, ammonium vanadate and potassium metavanadate. A solution of vanadium pentoxide in sodium hydroxide solution, eg. a 2–6% strength by weight solution of vanadium pentoxide in 10–20% strength by weight sodium hydroxide solution, has proven particularly useful. From 0.1 to 100, in particular from 0.5 to 50, ppm, calculated as vanadium, of water-soluble vanadium compounds are advantageously added to the scrubbing liquors. It has proven particularly useful to add the water-soluble vanadium compounds to the scrubbing liquors directly after the latter have been separated off from the cyclohexane oxidation mixture.

The treatment is carried out at from 50° to 130° C., in particular from 70° to 120° C., the stated temperatures advantageously being maintained for a residence time of from 15 to 90 minutes.

Aqueous solutions obtained by the process of the invention are useful, for example, for the preparation of hexanediol.

The Examples which follow illustrate the process.

EXAMPLE 1

Aqueous acidic scrubbing liquior obtained by washing a cyclohexane oxidation mixture with water at 120° C. under 15 bar and having an acid number of 90 is mixed with sodium vanadate so that the vanadium content is 10 ppm. The solution is heated at 100° C. for 30 minutes. Even after prolonged storage at 90° C., no hydrogen escapes from the solution treated in this manner.

EXAMPLE 2

Potassium metavanadate is added to an aqueous acidic scrubbing liquor as described in Example 1, in an amount such that the content of vanadium is 20 ppm. The solution is passed through a two-stage stirred kettle cascade at 100° C., the residence time in each stage being 30 minutes. No release of hydrogen from the resulting solution is observed.

COMPARATIVE EXAMPLE 1

The acidic scrubbing liquor described in Example 1 is used, and is kept at 80° C. In the course of from 20 to 40 hours, from 0.4 to 2.5 l of gas predominantly consisting of hydrogen and containing small amounts of carbon monoxide and carbon dioxide are released per kg of solution.

It is desirable to show, in a further comparative experiment, that other heavy metals do not have the desired effect.

COMPARATIVE EXAMPLE 2

The acidic scrubbing liquor described in Example 1 is used, and cobalt sulfate, manganese sulfate or potassium chromate is added so that the heavy metal content is 20 ppm in each case. The respective solutions are heated at 100° C. for 30 minutes.

Hydrogen escapes from the solution treated in this manner when the latter is stored at 90° C.

We claim:

1. A process for stabilizing an aqueous acidic scrubbing liquor resulting from the oxidation of cyclohexane with molecular oxygen or with a gas containing molecular oxygen in the liquid phase at from 130° to 200° C.

and under a pressure from 5 to 25 bar and scrubbing the oxidation mixture thus obtained with water and separation of an aqueous acidic scrubbing liquor so as to prevent the formation of hydrogen-containing gases, which process comprises adding a water-soluble vanadium compound to the scrubbing liquour and heating the scrubbing liquor to a temperature from about 50° to 130° C.

2. The process of claim 1 wherein the vanadium compound is present in an amount of from 0.1 to 100 ppm, calculated as vanadium.

3. The process of claim 1 wherein the vanadium compound is a solution of vanadium pentoxide in sodium hydroxide.

4. The process of claim 1 wherein the vanadium compound is added directly after the scrubbing liquor has been separated from the cyclohexane oxidation mixture.

* * * * *